United States Patent
Hong et al.

(10) Patent No.: US 10,625,264 B2
(45) Date of Patent: Apr. 21, 2020

(54) FITTED LID FOR MULTI-WELL PLATE

(71) Applicant: Corning Incorporated, Corning, NY (US)

(72) Inventors: Yulong Hong, Painted Post, NY (US); Elizabeth Tran, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 88 days.

(21) Appl. No.: 15/054,460

(22) Filed: Feb. 26, 2016

(65) Prior Publication Data

US 2016/0250632 A1 Sep. 1, 2016

Related U.S. Application Data

(60) Provisional application No. 62/121,846, filed on Feb. 27, 2015.

(51) Int. Cl.
*B01L 3/00* (2006.01)
*C12M 1/32* (2006.01)
*C12M 1/00* (2006.01)

(52) U.S. Cl.
CPC ......... *B01L 3/50853* (2013.01); *C12M 23/12* (2013.01); *C12M 23/38* (2013.01); *B01L 2200/025* (2013.01); *B01L 2200/0684* (2013.01); *B01L 2200/0689* (2013.01); *B01L 2200/141* (2013.01); *B01L 2200/142* (2013.01); *B01L 2300/046* (2013.01); *B01L 2300/048* (2013.01); *B01L 2300/0809* (2013.01);
(Continued)

(58) Field of Classification Search
CPC ...................... B01L 3/50255; B01L 2300/0829

USPC ................................................... 422/552, 553
See application file for complete search history.

(56) References Cited

U.S. PATENT DOCUMENTS 4,902,481 A * 2/1990 Clark ..................... B01D 61/18
210/335
5,056,427 A 10/1991 Sakabe et al.
(Continued)

FOREIGN PATENT DOCUMENTS

EP 1069181 1/2001
JP 2010233456 A 10/2010
(Continued)

OTHER PUBLICATIONS

Peterson. Development of aquatic plant bioassays for rapid screening and interpretive risk assessments of metal mining wastewaters. SRC (Saskatchewan Research Council) Publication No. E-2100-2-C95, Saskatchewan, Canada, 1995, 191.
(Continued)

*Primary Examiner* — Natalia Levkovich
(74) *Attorney, Agent, or Firm* — F. Brock Riggs

(57) ABSTRACT

A lid for a multi-well plate having apertures, each aperture having a gas permeable membrane, and fittings extending from the bottom surface of the lid to fit with a multi-well plate to reduce evaporation of liquid contents from within the wells of the multi-well plate, protect the contents of a multi-well plate from spilling or from mingling with the contents of a neighboring well in a multi-well plate is disclosed. The gas permeable membrane comprises one or more of (i) a continuous or discontinuous thin film associated with each aperture, (ii) a locally-thinned portion of the main body, and (iii) a quantity of material at least partially filling each aperture.

29 Claims, 12 Drawing Sheets

(52) U.S. Cl.
CPC .............. *B01L 2300/0829* (2013.01); *B01L 2300/0848* (2013.01); *B01L 2300/12* (2013.01)

(56) References Cited

U.S. PATENT DOCUMENTS

| | | | |
|---|---|---|---|
| 5,418,171 A * | 5/1995 | Kimura | B01L 3/5025 |
| | | | 422/408 |
| 5,604,130 A | 2/1997 | Warner et al. | |
| 5,665,247 A | 9/1997 | Valus et al. | |
| 5,721,136 A | 2/1998 | Finney et al. | |
| 5,741,463 A * | 4/1998 | Sanadi | B01L 3/5025 |
| | | | 422/527 |
| 5,780,294 A | 7/1998 | Stevens et al. | |
| 5,817,509 A | 10/1998 | Stevens et al. | |
| 5,853,586 A | 12/1998 | Valus et al. | |
| 5,863,792 A | 1/1999 | Tyndorf et al. | |
| 5,882,922 A | 3/1999 | Tyndorf et al. | |
| 6,027,694 A | 2/2000 | Boulton et al. | |
| 6,170,684 B1 | 1/2001 | Vincent et al. | |
| 6,251,662 B1 | 6/2001 | Day | |
| 6,426,205 B1 | 7/2002 | Tyers et al. | |
| 6,426,215 B1 | 7/2002 | Sandell | |
| 6,534,014 B1 | 5/2003 | Mainquist et al. | |
| 7,037,580 B2 | 5/2006 | Razavi et al. | |
| 7,125,522 B2 | 10/2006 | Hall | |
| 7,309,603 B2 | 12/2007 | Ma et al. | |
| 7,531,140 B2 | 5/2009 | Szlosek | |
| 8,906,685 B2 | 12/2014 | Takayama et al. | |
| 8,999,703 B2 | 4/2015 | Welch et al. | |
| 2001/0007642 A1 | 7/2001 | Feiglin | |
| 2001/0024821 A1 | 9/2001 | Potter | |
| 2002/0054833 A1 | 5/2002 | Qu et al. | |
| 2002/0083686 A1 | 7/2002 | Audino et al. | |
| 2004/0115798 A1 | 6/2004 | Ma et al. | |
| 2008/0003670 A1 | 1/2008 | Martin et al. | |
| 2010/0202927 A1 | 8/2010 | Queeney et al. | |
| 2014/0322806 A1 | 10/2014 | Bennett et al. | |

FOREIGN PATENT DOCUMENTS

| | | |
|---|---|---|
| WO | 1995027196 | 10/1995 |
| WO | 2004022235 | 3/2004 |
| WO | 2008134748 A1 | 6/2008 |

OTHER PUBLICATIONS

U.S. Appl. No. 10/319,75, filed Dec. 13, 2002; U.S. Pat. No. 7,309,603.

International Search Report and Written Opinion PCT/US2016/019684 dated May 19, 2016.

Japanese Patent Application No. 2017545313; Machine Translation of the Office Action dated Jan. 8, 2020; Japan Patent Office; 5 Pgs.

* cited by examiner

FITTED LID FOR MULTI-WELL PLATE

This application claims the benefit of priority under 35 U.S.C. § 119 of U.S. Provisional Application Ser. No. 62/121,846 filed on Feb. 27, 2015 the content of which is relied upon and incorporated herein by reference in its entirety.

BACKGROUND

Field

The present disclosure relates generally to lids for multi-well plates, and more specifically to fitted lids having gas permeable material and fittings to fit with a multi-well plate.

Technical Background

Recent advancements in many areas of biotechnology have increased the demand to perform a variety of assays in both biological and chemical systems. These assays include for example, biochemical reaction kinetics, DNA melting point determinations, DNA spectral shifts, DNA and protein concentration measurements, excitation/emission of fluorescent probes, enzyme activities, enzyme co-factor assays, homogeneous assays, drug metabolite assays, drug concentration assays, dispensing confirmation, volume confirmation, solvent concentration, and solvation concentration. There are also a number of assays that use intact living cells and which may include visual examination.

Assays of biological and chemical systems are carried out on a large scale in both industry and academia. It is desirable to have an apparatus for performing these studies in a convenient and economical fashion. Because they are relatively easy to handle, low in cost, and disposable, multi-well plates (also called microplates) are often used for such evaluations. Multi-well plates typically are formed from a polymeric material and include an ordered array of individual wells. The wells may be arranged in an array of mutually perpendicular rows and columns. Each well includes sidewalls and a bottom so that an aliquot of sample may be retained within each well. Common multi-well plates include well arrays having standardized dimensions of 8×12 (96 wells), 16×24 (384 wells), and 32×48 (1536 wells) though other sizes are used.

Multi-well plates may be used in conjunction with a lid (or cover) to maintain sterility within the wells and minimize evaporation. Such lids, which are typically made from hard plastic and are configured to fit over the plates to exclude contamination, generally fit loosely on top of and around the multi-well plate. When a covered multi-well plate is placed within an incubator or even on a countertop, evaporation of the liquid contents, especially for multi-well plates where the number of wells is 1536 or greater (and the volume of liquid in each well is small), can exceed 15% to 25%, particularly for the corner wells and the wells located at the periphery of the plate. This high amount of evaporation can cause unacceptable changes in pH, nutrient content, salt concentration, etc. In addition, the rate of gas exchange can also be greater at the perimeter than at the plate center. These "edge effect" phenomena are not only detrimental to assay samples, but also negatively impact reproducibility among the various wells in a given microplate. Further, well-to-well cross-contamination can occur due to the migration of aerosols formed during agitation of the plate or condensate formed on the underside of the lid.

Sealing tape and other supplemental films, foils and mats have been used to prevent evaporation and edge effect. However, many such products are not effective at protecting against evaporation and are not automation friendly with the high throughput screening (FITS) procedures used in many laboratories.

In view of the foregoing, there is a need to provide a multi-well plate lid that can reduce evaporation and edge effect while improving gas exchange and limiting the risk of well-to-well cross-contamination. It is also desirable to provide a lid that is inexpensive to manufacture, easy to manipulate both by hand and robotically, and compatible with the needs of HTS.

BRIEF SUMMARY

In accordance with embodiments of the present disclosure, a lid for a multi-well plate is disclosed herein. In embodiments, the lid has apertures, each aperture having a gas permeable membrane, and fittings extending from the bottom surface of the lid structured to fit with a multi-well plate, and to create a conduit for gas exchange into and out of each well through the lid, and also structured to reduce evaporation of liquid contents from within the wells of the multi-well plate and to protect the contents of a multi-well plate from spilling or from mingling with the contents of a neighboring well in a multi-well plate. The gas permeable membrane comprises one or more of (i) a continuous or discontinuous thin film associated with each aperture, (ii) a locally-thinned portion of the main body, and (iii) a quantity of gas permeable material at least partially filling each aperture.

In embodiments, the lid is re-usable and automation-friendly and, during use, limits inter-well cross-contamination, enables consistent gas exchange into and out of each of the plurality of wells, and minimizes evaporation of the well contents from within the wells. Gaseous species include oxygen, carbon dioxide, nitrogen and ammonia.

An example lid comprises a main body having top and bottom surfaces, a skirt extending downwardly from the perimeter of the body, an array of fittings projecting from the bottom surface of the lid, the fittings configured to engage with well openings of a multi-well plate, and a gas permeable membrane formed in the main body, associated with each aperture. Each of the semipermeable membranes corresponds to a respective one of the plurality of well apertures in the lid, and each aperture of the lid associates with a top opening of a well of a microplate.

In embodiments the lid main body is a rigid, unitary structure. A rigid structure, as opposed to a flexible material, is amenable to robotic handling and high throughput screening. Each semipermeable or gas permeable membrane may be formed from the lid body material, or may comprise a different material. In embodiments, the semipermeable membrane may comprise a plug, a sheet of continuous thin film or a discontinuous sheet of thin film. In embodiments, a plurality of apertures is associated with the fitting. In embodiments, the gas permeable membrane may comprise a gas-permeable, non-wetting thin film.

In embodiments, the disclosure provides a multi-well plate lid having a unitary rigid main body having a top surface, a bottom surface, and a plurality of apertures in the main body; each aperture having a gas permeable material and an associated fitting, each fitting having an end face or distal face and fitting walls; wherein fittings extend from the bottom surface of the main body; wherein each fitting is structured to fit with a well of a multi-well plate; and wherein the diameter of each aperture (Da) is smaller than the distance between fitting walls (Df). The fitting walls are the walls of the fittings that engage with the wells of a multi-well plate, whether the engagement occurs against the inside of a well of a multi-well plate or against the outside of a well of a multi-well plate. The fitting wall may fit against the outside of a well when, for example, the top ring of a well extends above the plane of a multiwell plate (see, for example, U.S. Pat. No. 7,531,140). The term "fittingly engaged" means that the fitting fits snugly within or around the top of a well, so that a friction fit is formed between the fittings of the lid, or the fitting walls of the lid, and the well opening.

In embodiments, the lid may have fittings structured to fit around or inside a well of a multi-well plate. The end faces or distal ends of the fittings may be shaped, that is they may be convex, concave or flat, or any other shape. In embodiments, there may be more than one aperture associated with each fitting. That is, there may be a cluster of apertures for each fitting, associated with a single well of a multi-well plate. And, in embodiments, some wells of the plate may not have an associated aperture. For example, some wells may be control wells that do not allow for gas exchange through an aperture. Or, for example, some wells may not require gas exchange, so the lid may have apertures that correspond to less than the total number of wells in the associated multi-well plate.

In embodiments, the gas permeable membrane may be a continuous thin film covering a majority of the top surface of the main surface of the lid, a discontinuous thin film covering each aperture at the top surface of the planar main surface of the lid, a plug of gas permeable material in each aperture, or a combination. The gas permeable material may be on the top surface of the lid, on the bottom surface of the main body of the lid, or inside the apertures. In embodiments, the lid has a stacking feature on the top surface of the lid to enable the lid to stack with another multi-well plate. A polymer mesh may also be present.

In embodiments, the lid is made from stainless steel, glass, ceramic, or a polymer material selected from the group consisting of polystyrene, polymethylpentene, polypropylene, polyethylene, polytetrafluoroethylene, polycarbonate, and polyacrylate. In embodiments, the lid is made from a polymer material and the gas permeable material is a locally-thinned layer of the same polymer material. In embodiments, the lid, including the gas permeable material, is a single-shot part. In embodiments, the lid and the multi-well plate are sealed together.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
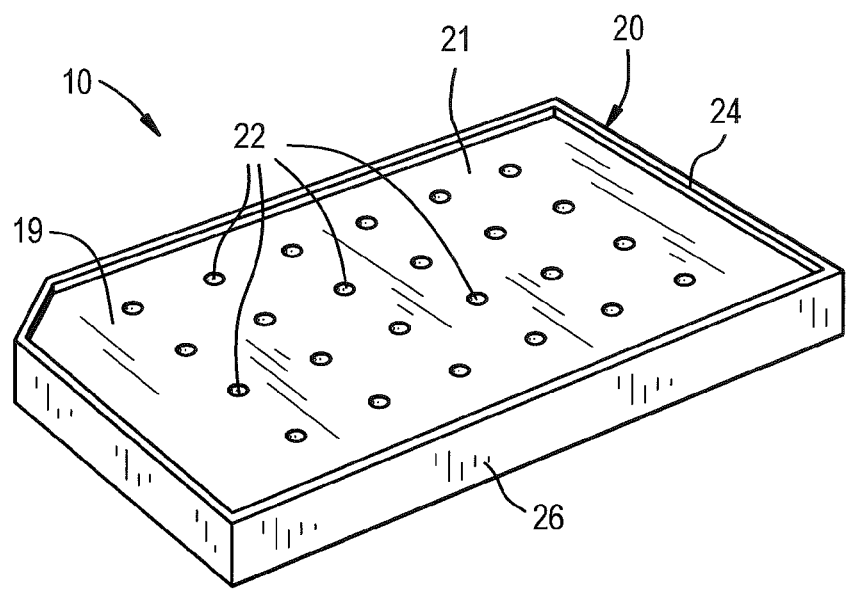
FIG. 1A is an exploded perspective view of a multi-well plate and lid according to one embodiment.

Reference will now be made in greater detail to various embodiments of the subject matter of the present disclosure, some embodiments of which are illustrated in the accompanying drawings. The same reference numerals will be used throughout the drawings to refer to the same or similar parts.

Disclosed is a lid for sealing and allowing gas exchange in a multi-well plate. An assay or cell culture device comprising such a lid is shown in FIG. 1. The device is referred to as an assay device when used for assays or testing. In embodiments, the device is referred to as a cell culture device when used, for example, for cell culture.

When a multi-well plate is used for assays, several features are desirable. For example, in embodiments, the device can contain fluid or liquid in a way that minimizes the risk that the fluid will spill, minimizes the risk that the contents of one well will cross over into another well (minimizing the risk of cross-contamination) and limits evaporation from the wells.

In some prior art devices, loose lids allow for evaporation to occur unevenly across wells in a multi-well plate. Often, wells at the periphery of a multi-well plate or in the corners of a multi-well plate, experience more evaporation than wells in the interior of an array of wells. This uneven evaporation can result in assay results that are inconsistent due to increased concentration of reagents in peripheral wells. In embodiments, it is desirable that, even if evaporation may occur, evaporation occurs evenly in each well. In embodiments, the device containing liquid is structured to ensure that evaporation will occur evenly across the wells of a multi-well plate. This ensures that results of an assay will be more uniform, more controlled.

In addition, in embodiments, it is desirable that the lid remain in place during use. In some uses, including uses that require mixing or shaking, multi-well plates may undergo significant agitation. Some prior art devices ensure that the lid will stay in place by providing a separate lock device such as, for example, a clamp or a screw and bolt connection. In embodiments, it is desirable that the device be easily used, without the use of additional hardware such as clamps, bolts, screws, adhesives, heat or other mechanisms to ensure that the lid remains on the multi-well plate.

When a multi-well plate is used for cell culture, additional features are desirable. Cells in culture require nutrients, oxygen and an environment that minimizes the risk of contamination. For example, during cell culture it is desirable to provide gas exchange to the fluid inside a well. It is also desirable that the gas exchange provided through the lid is limited, in order to limit evaporation from the contents of a well.

In embodiments, it is desirable that the use of the device does not require assembly of multiple pieces and parts to achieve the desired features of the container. For example, it may not be desirable to require the user to assemble the multi-well plate together with inserts that must be placed into the multi-well plate, covered by a gasket, and then covered by a lid. Each of these assembly steps takes time and has a risk of contamination or that the device may be assembled incorrectly. In addition, each of these assembly steps, which introduces a separate part into the multi-well plate system, incurs a risk of contamination if the device is to be used in cell culture. In embodiments, it is desirable to have a single lid that can simply be placed on a multi-well plate, and removed from a multi-well plate. It is also desirable that a multi-well plate and lid be amenable to multiple uses. In embodiments, it may be easier to control inventory of laboratory equipment if one device can be used interchangeably as an assay container and as a cell culture container. This is especially true when the assay being performed requires cell culture.

It is also desirable to provide a device that is relatively easy to manufacture and uses a minimum of materials and manufacturing steps. Multiple materials, multiple assembly or manufacturing steps, and complex structure lead to more expensive devices. In embodiments, it is desirable to provide a less expensive device to manufacture.

FIG. 1A is an exploded perspective view of a multi-well plate 12 and lid 20 (together, 10) according to an embodiment. FIG. 1A illustrates a lid 20 and a multi-well plate 12. In embodiments, lid 20 is a unitary rigid main body having a top surface 21 and a plurality of apertures 22 through the main body 19. Lid also has a skirt 26 which can be any length (short, medium, or long). In embodiments, lid has a raised peripheral edge 24. Lid is illustrated in more detail in FIG. 2. Lid is structured to fit with the wells of multi-well plate 12, as shown in FIG. 1B.

Also show in FIG. 1A, multi-well plate 12 has a frame 14 and a plurality of wells 15 arranged in an array. The wells 15 include peripheral wells arranged adjacent to the frame 14. Each well has well walls 40. The plate 12 dimensionally conforms to industry standard footprints for multi-well plates. In an example plate, the width and length dimensions are standardized at approximately 85 mm and 128 mm, respectively.

Figure 1B:
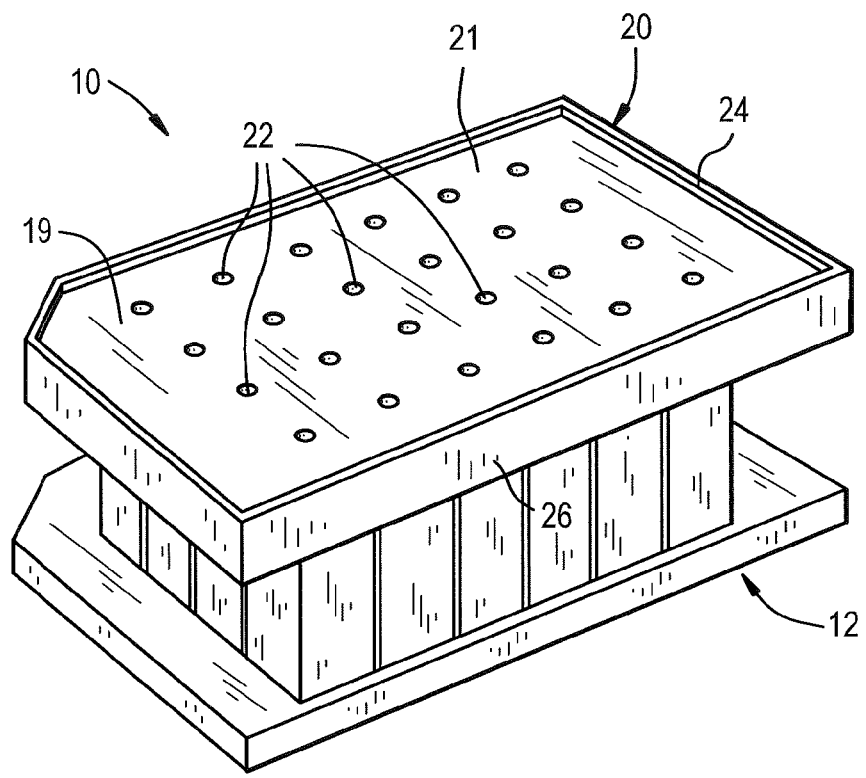
FIG. 1B is a perspective view of the multi-well plate with the lid attached, according to embodiments.

FIG. 1B illustrates the lid 20 engaged with a multi-well plate, in an embodiment. FIG. 1B illustrates the lid 20, having a plurality of apertures 22 in the main body 19 of the lid and a peripheral skirt 26. The lid fits with the multi-well plate 12. The apertures can be any shape or size.

Figure 2:
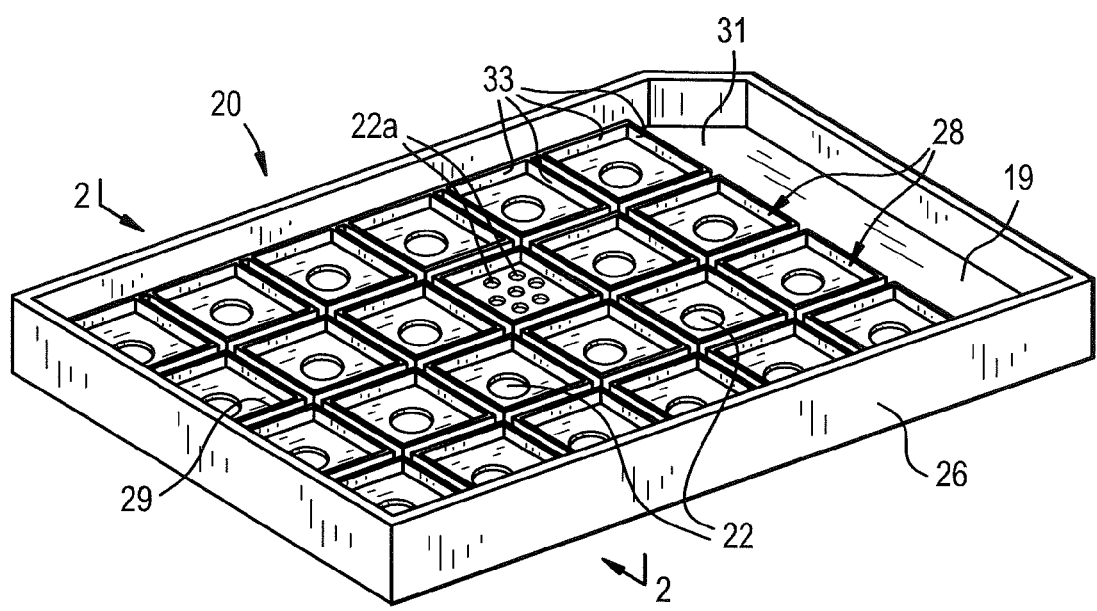
FIG. 2 is a schematic view showing the underside of a lid showing apertures and fittings according to embodiments.
Figure 10A:
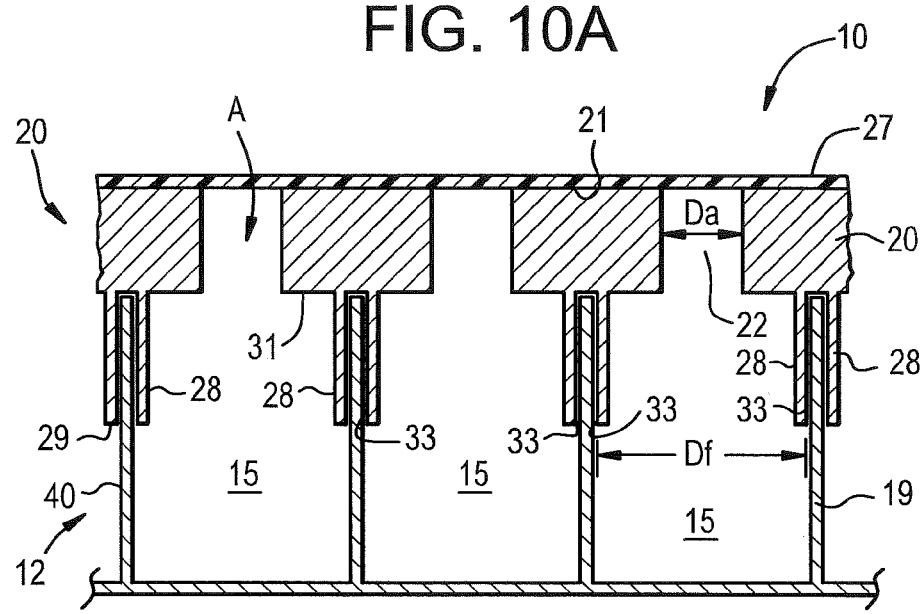
FIGS. 10A and 10B are cross-sectional views of a multi-well plate covered by a lid according to embodiments.
Figure 10B:
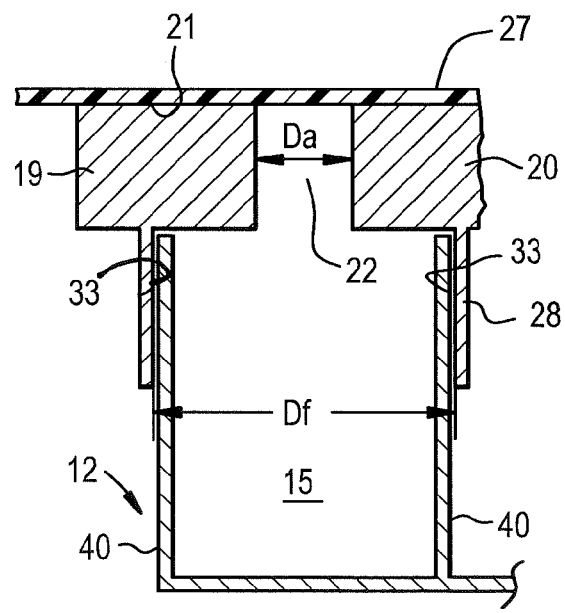

FIG. 2 is a schematic view showing the underside of a lid 20 showing fittings 28 according to one embodiment. In embodiments, lid 20 is a unitary, rigid structure having a planar main body 19 which has a top surface (21 shown in FIG. 1A), a bottom surface 31, apertures 22 through the main body 19 and fittings 28 extending from the bottom surface 31 of the main body wherein each fitting is structured to fit with a well 15 of a multi-well plate 12 (see FIG. 1A). In embodiments, fittings 28 are round, square or any other shape and are structured to form a seal with wells of a multi-well plate, which can be round, square, or any other shape. In embodiments, the fittings may form a seal around the top of wells of a multi-well plate (as shown in FIG. 10B, for example) or inside the top of wells of a multi-well plate (as shown in FIG. 10A). In embodiments the fittings 28 have a distal end face 29 (see, for example, FIGS. 12, 14 and 16) which can be flat, concave, convex or any other shape. Fittings also have fitting walls 33 for fitting with the walls of a multi-well plate. This closure mechanism provides several advantages. By forming a seal at the top of each well, the lid provides containment of liquid inside the well in a way that minimizes the risk that the fluid will spill. Because a separate seal is made at the top of each well individually, the presence of fittings, structured to fit with individual wells of a multi-well plate, minimizes the risk that the contents of one well will cross over into another well (minimizing the risk of cross-contamination). The seal at the top of the well also minimizes evaporation from the wells. Because each well has a seal at the top, each well experiences the same conditions, so that even if there is evaporation, each well will experience that evaporation similarly. And, these multiple fittings, one for each well of the microplate, functions to seal the lid onto the microplate so that the lid is not loose or easily dislodged from the microplate. FIG. 2 also illustrates that, in embodiments, each fitting may have multiple apertures 22a associated with each fitting. FIG. 2 also illustrates a skirt 26 extending from the main body 19 along the periphery of the main body 19.

The lid 20 is dimensioned to cover the multi-well plate 12, and may be made from a rigid, non-flexible material such as stainless steel, glass, plastic or ceramic. A rigid lid, instead of a flexible or elastomeric lid, may be more amenable to robotic handling, stacking and high throughput screening. In embodiments, the lid is made of a moldable and/or printable plastic. Examples of moldable plastics include, but are not limited to polystyrene, polymethylpentene, polypropylene, polyethylene, polytetrafluoroethylene, polycarbonate, and polyacrylate. The lid may be made of a material that is durable and resistant to chemical solvents and reagents, i.e., able to withstand high humidity and gaseous environments, such as inside a humidified, $CO_2$ incubator.

Apertures 22, present in the lid, provide for gas exchange with the associated well of a multi-well plate, making this device amenable for use as a cell culture container as well as a storage or assay container. In embodiments, not all of the wells of the multi-well plate have an associated aperture. In embodiments, apertures may have associated gas permeable membrane or may not have associated gas permeable membrane. In embodiments, the apertures are filled with or covered by gas permeable membrane. As used herein, a gas permeable membrane, also termed a selectively permeable membrane, a partially permeable membrane, a semipermeable membrane or a differentially permeable membrane (all with the same meaning), is a barrier that allows certain molecules to pass through it by diffusion. The rate of passage depends, inter alia, on the pressure, concentration, and temperature of the molecules on either side of the membrane, as well as the permeability of the membrane to each molecule. Depending on the membrane and the molecule, permeability may depend on molecule size, solubility, properties, or chemistry. As disclosed in various embodiments herein, the semipermeable membrane may allow gasses but not liquids to pass through. In embodiments, the gas permeable membrane is formed integrally with the lid or added to or affixed to the lid as a discontinuous thin film, a continuous thin film or a plug.

FIGS. 3-9 are schematic cross-sectional views, taken at line 2-2 of FIG. 2 of lids according to further embodiments, showing different configurations of fittings 28 and apertures 22. In embodiments, each aperture has a gas permeable membrane. In embodiments, each aperture does not have a gas permeable membrane. Or, in embodiments, a subset of apertures has a gas permeable membrane. In the case of the lid, each aperture defines an opening in the main body 19 to allow fluid communication between the top surface 21 and the bottom surface 31 of the main body, or between the top surface 21 and the area between fittings 28, as illustrated by arrow A in FIG. 3. When the lid is engaged with a multi-well plate, each aperture defines an opening in the main body 19 to allow fluid communication between the external environment and the interior of a well of a multi-well plate (as shown, for example, in FIG. 10), as shown by arrow A. In the embodiment illustrated in FIG. 3, the gas permeable material is a gas permeable membrane or layer 27 adjacent to the top surface 21 of the main body 19 of the lid. However, in embodiments, gas permeable material 27 may be adjacent to the top surface 21, (see for example, FIG. 3) adjacent to the bottom surface 31 of the main body (see, for example, FIG. 8 and FIG. 9), may fill the aperture as a plug 25 (see, for example, FIG. 5), may be continuous across a surface of the main body (see, for example, FIG. 3 and FIG. 8) or may be discontinuous across a surface of the main body (see, for example, FIG. 7 and FIG. 9). Discontinuous means that gas permeable membrane may be present in or on the lid, covering one aperture or more than one apertures, but not covering the entire main body of the lid. Gas permeable material may be a sheet or film of material (as shown in, for example, FIG. 3) or gas permeable material may be a plug 25 of material inside aperture 22 (as shown, for example, in FIG. 5 and FIG. 6) or a locally thinned area of material 23 inside aperture 22 (as shown, for example, in FIG. 4). In embodiments, the device comprises a combination of a layer of gas permeable material and gas permeable material as a plug in the aperture 22, as shown as 25 and 27 in FIG. 6.

Figure 3:
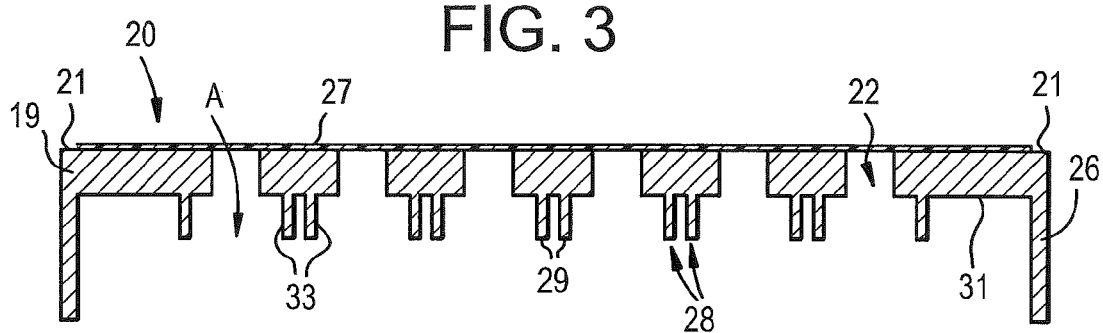
FIGS. 3-9 are schematic cross-sectional views taken at line 2-2 shown in FIG. 2, of lids according to further embodiments.

In the embodiment shown in FIG. 3, a gas permeable membrane 27 is illustrated on the top surface of the main body 19. In embodiments, that gas permeable membrane may be affixed to the top surface of main body 19 by any methods known in the art including heat welding, laser welding, pressure bonding, adhesive bonding, ultrasonic welding, or any other method to form an integral part. FIG. 3 also shows fittings 28 extending from the bottom surface 31 of the main body 19, structured to engage with or fit with a well of a multi-well plate (see, for example, FIG. 11).

Figure 4:
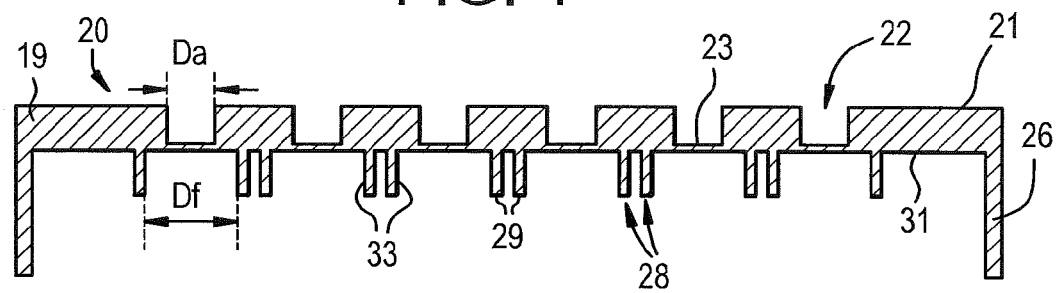
Figure 13:
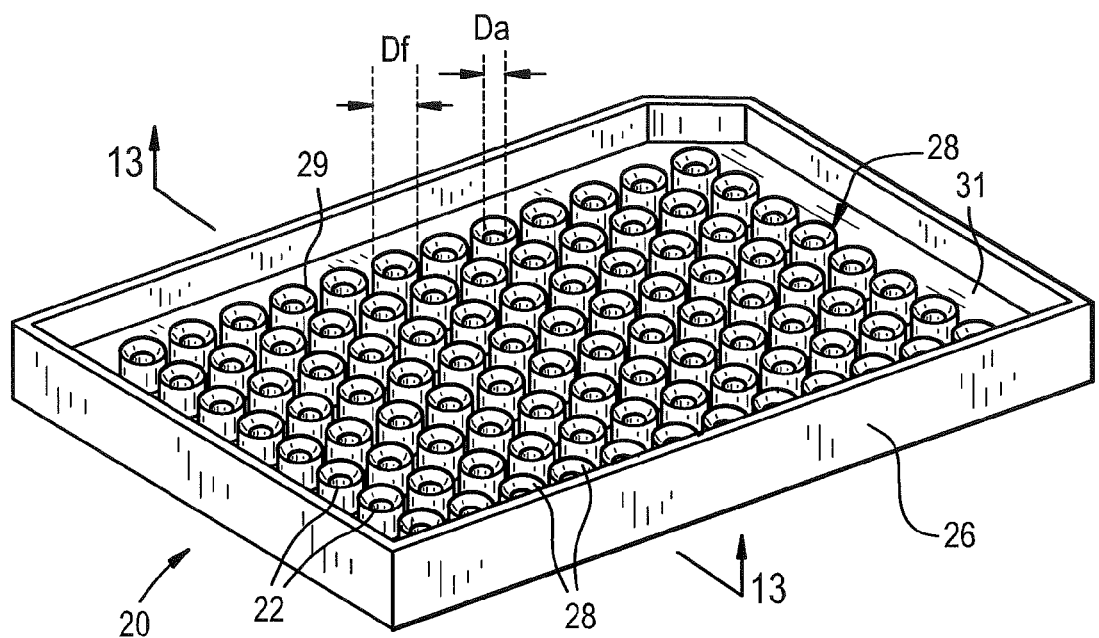
FIG. 13 is a perspective view of the underside of a lid according to an embodiment.
Figure 15:
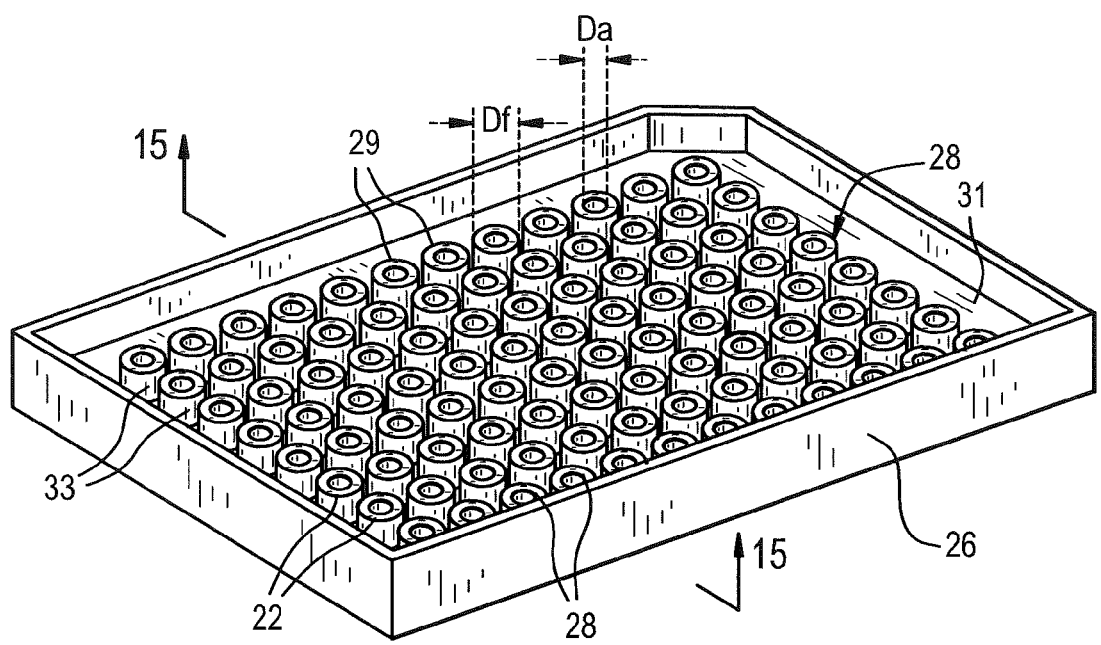
FIG. 15 is a perspective view of the underside of a lid according to an embodiment.

Each fitting 28 has an end face or distal face 29 and fitting walls 33. End faces or distal faces can be any shape. As shown in FIGS. 13, 15 and 17, the distal face can be convex, concave or flat, or any combination of these shapes, or any other shape. Fittings are structured to engage with the wells of a multi-well plate (see, for example, FIG. 10) by forming a friction fit between the fitting wall 33 and the well of a multi-well plate. As shown in FIG. 4, the diameter of the apertures (Da) is smaller than the distance between the fitting walls (Df) to minimize evaporation from wells. In embodiments, the fitting is structured to fit inside a well of a multi-well plate (FIG. 10A). In embodiments, the fitting is structured to fit around a wall of a multi-well plate, see FIG. 10B. For example, the well may have a raised top ring of a well which extends above the plane of a multiwell plate (see, for example, U.S. Pat. No. 7,531,140). The term "fittingly engaged" means that the fitting fits snugly within or around the top of a well, so that a friction fit is formed between the fitting wall or walls 33 of the fittings 28 of the lid 20 and the well opening 15.

Because evaporation can occur wherever there is gas exchange (for example, wherever there is gas permeable material that allows gas to pass through the lid, as shown by arrow A in FIG. 3), keeping the diameter of the apertures small in relation to the distance between fittings (which relates to the diameter of the well opening) minimizes the evaporation that can occur from liquid contained in a well of a multi-well plate.

FIG. 4 is a cross-sectional view of a lid comprising a locally-thinned thin wall 23 across the aperture 22 according to one embodiment. In the embodiment shown in FIG. 4, the locally thinned thin wall 23 is thin enough to be gas permeable material. In this embodiment, the lid 20 is molded as a single part in a single shot molding process. Because the thin wall 23 at the bottom of the aperture 22 (the thin wall 23 may also be a the top of the aperture or within the aperture, in embodiments) is thin enough to be gas permeable, the lid allows gas exchange across the thin wall and therefore to and from the wells 15. This thin gas permeable wall also controls and minimizes evaporation from the wells 15 (not shown, but see for example, FIG. 10).

In embodiments, the locally-thinned portion may be flush with the lid top surface 21, the lid bottom surface 31 (as illustrated) or lie intermediate to the top and bottom surfaces. In the illustrated embodiment, the membrane material is formed from the same material as the lid, e.g., polystyrene, polymethylpentene, polypropylene, polyethylene, polytetrafluoroethylene, polycarbonate, or polyacrylate, and the thin wall 23 is formed at the bottom of apertures 22. The lid may configured such that for each well 15, one or more corresponding apertures 22 are provided (e.g., 1, 2, 3, 4 or 5 lid openings per well (See 22a in FIG. 2)).

In embodiments, the gas permeable membrane may be a continuous thin film covering a majority of the top surface of the main surface of the lid, a discontinuous thin film covering each aperture or a small group of apertures at the top surface of the planar main surface of the lid, a plug of gas permeable material in each aperture, or a combination. The gas permeable material may be on the top surface of the lid, on the bottom surface of the main body of the lid, or inside the apertures. However, the gas permeable material is not on the end face or distal end of the fittings. In embodiments, it is desirable to minimize contact between the contents of a multi-well plate and the semipermeable or gas permeable membrane. If the gas permeable membrane is at the distal end or end face of the fittings, there is an increased probability that the contents of the wells will come in contact with the membrane. If this occurs, there is some risk that the membrane may become plugged (by salts in the media or liquid contents of the well) or contaminated by the contents of the well.

Figure 5:
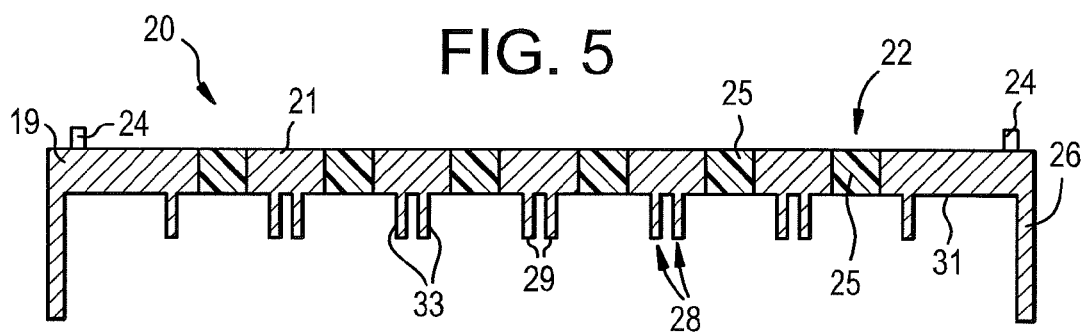

FIG. 5 is a cross-sectional view of a lid comprising a gas plug of permeable material 25 filling apertures 22. In this embodiment gas permeable material extends from the top surface 21 to the bottom surface 31 of the lid main body 19. Gas permeable material 25 may be a material that is different from the material used to form the lid, and which is added to the lid after forming the lid. That is, the lid itself, having a unitary rigid main body having a top surface, a bottom surface and a plurality of apertures through the main body, each aperture having an associated fitting extending from the bottom surface of the main body, wherein each fitting is structured to fit with a well of a multi-well plate. In embodiments, the lid may be made in a single-shot molding process or may undergo additional manufacturing steps which include adding gas permeable material associated with the apertures. For instance, the lid may be formed with or otherwise provided with one or a plurality of apertures which is/are at least partially filled with a semipermeable membrane material 25. In embodiments, the semipermeable membrane may be integral to the lid, i.e., not readily separable or detachable therefrom. Or, in embodiments, the gas permeable material may be removable. Examples of such materials, which may be incorporated into the lid using, for example, an over-molding process include polystyrene, polymethylpentene, polytetrafluoroethylene, polycarbonate, polyacrylate, polyurethane, non-woven rayon, ethyl cellulose, perforated acetate and polyester. Apertures 22 in the lid may or may not be aligned with a center of a well opening. FIG. 5 also illustrates optional raised peripheral edge 24. Raised peripheral edge allows a second multi-well plate to stack on top of a lid 10.

Figure 6:
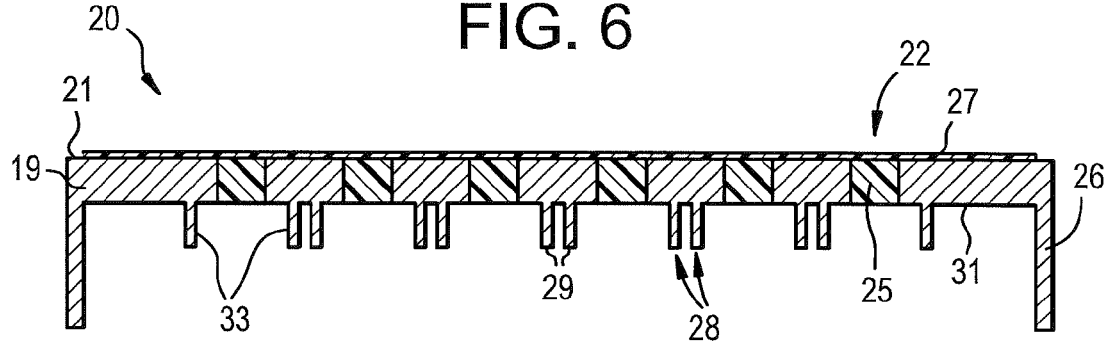

In embodiments, the aperture 22 contains, or is covered by, on the top side or the bottom side, gas permeable material. Illustrated schematically in FIG. 6 is a cross-sectional view of a lid comprising a main body 19 having a top surface 21 and a bottom surface 31, apertures 22, fittings 28 extending from the bottom surface of the main body, and also having a semipermeable or gas permeable material 25 filling apertures and further comprising a continuous thin film 27 covering a majority of the top surface 21 of the lid. As shown in FIG. 6, the lid has a plurality of openings 22 through the main body 19 of the lid 20 arranged to each align with a respective one of the well openings, as well as fittings 28 extending from the bottom surface 31 of the main body 19 of the lid 20, structured to fit with a well of a multi-well plate. Fittings have fitting walls 33 and end faces or distal faces 29. As in the embodiment of FIG. 5, the openings are at least partially filled with a semipermeable or gas permeable material 25 different from the material used to form the lid. Further, as shown in FIG. 6, each filled opening is covered with at least one gas-permeable thin film 27. In embodiments the gas permeable thin film 27 is non-wettable or waterproof.

Figure 7:
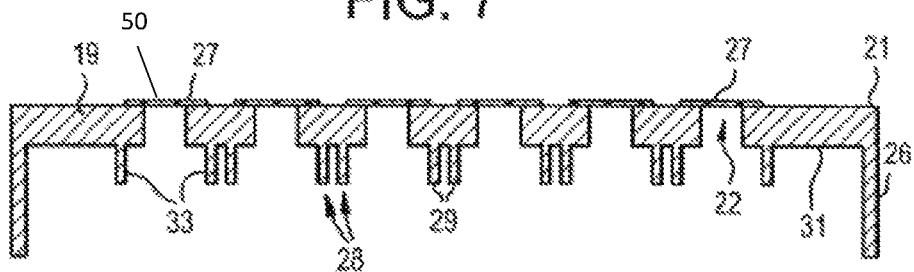
Figure 8:
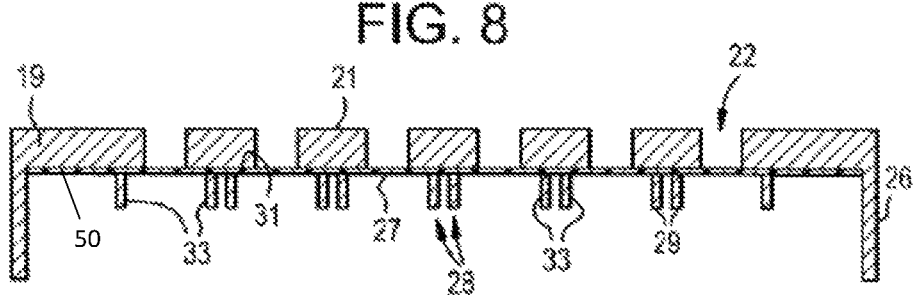
Figure 9:
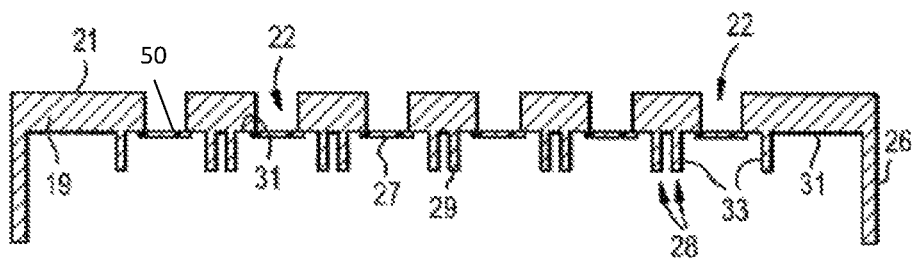
Figure 18:
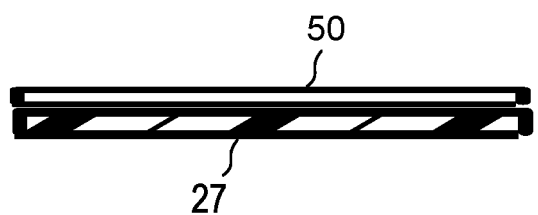
FIG. 18 is a close-up cross-sectional view of the gas permeable material and polymer mesh of FIG. 7.

In embodiments, such as that shown, for example, in FIG. 7, the thin film 27 may be discontinuous, but still covering apertures. As illustrated in FIG. 6, the thin film 27 is affixed to the top surface 21 of the lid. However, the film can alternatively be attached to the bottom surface 31 (see FIG. 8 and FIG. 9) of the lid. When affixed to the bottom surface 31 of the lid 20, the thin film of gas permeable material 27 may be continuous (as shown in FIG. 8 or discontinuous (as shown in FIG. 9). In embodiments where a thin film membrane is provided, the openings may be unfilled (e.g., free of semipermeable material 25) as shown in FIGS. 7, 8 and 9 or filled as shown in FIG. 6. In embodiments, a single thin film membrane covers all of the openings. In embodiments, the continuous thin film covers a majority (i.e., greater than 50%) of the top or bottom surface. In embodiments the gas-permeable thin film 27 can include a single layer film or a multi-layer film. In embodiments, multi-layer film means a composite thin film having two or more integral sub-layers that are not separable. In additional embodiments, the single layer film or multi-layer film may be covered by a polymer mesh 50 to protect the gas permeable membranes from direct contact during handling (see FIG. 18, which shows a close-up of the polymer mesh 50 on the gas-permeable thin film 27 of FIG. 7). As with the single layer film or multi-layer film, the polymer mesh 50 may be continuous or discontinuous. The polymer mesh 50 may be made of polyester.

As with the other semipermeable membrane materials, the thin film is permeable to gases such as oxygen, carbon dioxide, nitrogen and ammonia, but resistant to and substantially impermeable to water vapor. In embodiments, the thin film is also chemically resistant to solvents such as dimethyl sulfoxide, methanol, ethanol, dimethyl formamide, and dimethoxyethane.

The thin film can be made of any gas-permeable material. Example thin film materials that may be used to form a semipermeable membrane include silicone, polystyrene, polyethylene, polyester, polymethylpentene, polytetrafluoroethylene, polycarbonate, polyacrylate, polyurethane, nylon, non-woven rayon, ethyl cellulose, cellulose acetate. Such films may be non-porous, porous or perforated. Further example thin film materials include porous polymers, porous ceramic and porous glassy materials. In embodiments, the thin film has an average (or maximum) pore size no greater than 0.2 µm. In embodiments the gas permeable material is the same material as the lid, but thin enough to be gas permeable.

The thin film may be attached to top (or bottom) surface of the lid by use of a solvent-resistant adhesive, such as glue or double-sided adhesive tape. Example methods for forming and attaching the thin film to the lid include, but are not limited to injection molding, over-molding, thermoforming, vacuum forming, adhesive bonding, chemical bonding, thermal bonding, pressure bonding, ultrasonic bonding, mechanical bonding, and combinations thereof.

FIG. 10A a cross-sectional view of a multi-well plate 12 covered by a lid 20 according to the embodiment illustrated in FIG. 2. FIG. 10 shows walls 40 of a multi-well plate 12 engaged with fittings 28 of the lid 20. In the embodiment shown in FIG. 10, a thin film of semi-permeable or gas permeable material 27 covers the top surface 21 and the apertures 22 of the lid 20.

FIG. 10A also shows that the diameter of the apertures 22 (Da) is smaller than the distance between fitting walls 33. In the embodiment shown in FIG. 10A, fitting walls fit inside the wells 15 of the multi-well plate. That is, fitting walls 33 fit against and form a frictional seal with well walls 40.

In the embodiment shown in FIG. 10B, fittings 28 fit outside or around walls of the multi-well plate. That is, fitting walls 33 fit against, and form a frictional seal with, well walls 40. In either embodiment, Df is the distance between fitting walls 33. Fitting walls are the walls of the fittings 28 that form a frictional seal against a wall 40 of a multi-well plate.

Figure 11:
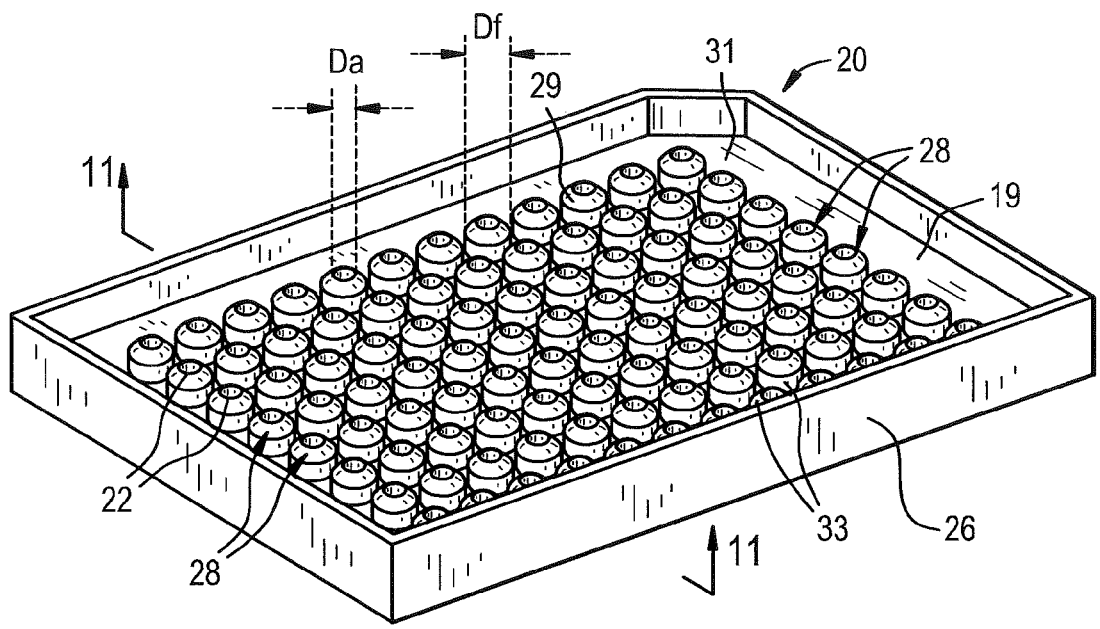
FIG. 11 is a perspective view of the underside of a lid according to an embodiment.
Figure 12:
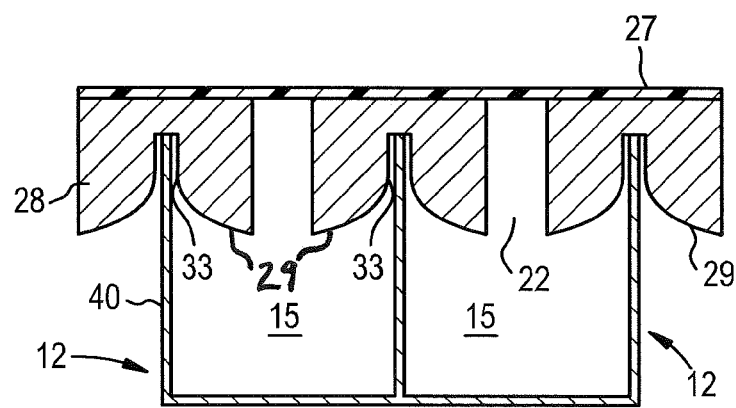
FIG. 12 is a cross-sectional view taken at line 11-11, of the lid shown in FIG. 11 engaged with a multi-well plate.

FIG. 11 is a perspective view of the underside of a lid 20 according to an embodiment. In this embodiment, the distal ends 29 of the fittings 28 are concave. FIG. 12 is a cross-sectional view of the lid shown in FIG. 11 engaged with well walls 40 of wells 15 of a multi-well plate 12, showing concave distal ends 29 of the fittings 28 and apertures 22. FIG. 12 is a cross-sectional view taken at line 11-11, of the lid shown in FIG. 11 engaged with a multi-well plate. In the embodiment shown in FIG. 11 and FIG. 12, the fittings are round and structured to fit inside round wells 15 of a multi-well plate. As can be seen in FIG. 11, Da, the diameter of apertures 22 is smaller than Df, the distance between fitting walls 33 of a fitting 28. Distance between fitting walls Df can also be considered to be the diameter of a fitting, in the embodiments shown in FIGS. 11, 13 and 15.

Figure 14:
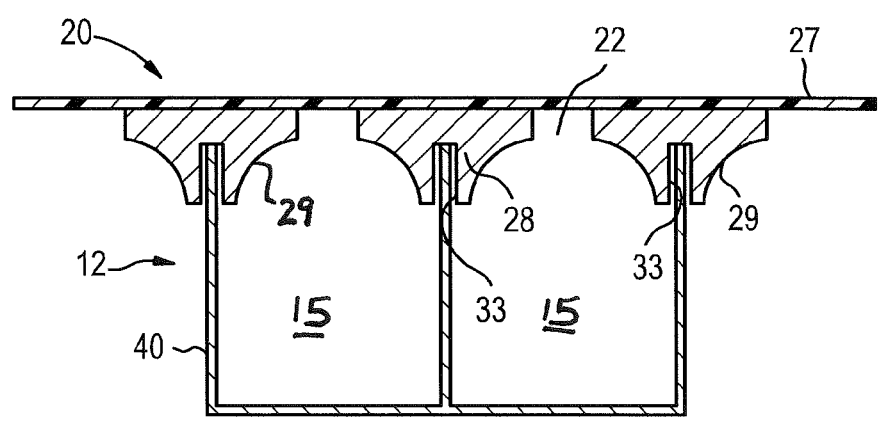
FIG. 14 is a cross-sectional view taken at line 13-13 of the lid shown in FIG. 13 engaged with a multi-well plate.

FIG. 13 is a perspective view of the underside of a lid 20 according to another embodiment. In this embodiment, the distal ends of the fittings 28 are convex. FIG. 14 is a cross-sectional view taken at line 13-13 of the lid 20 shown in FIG. 13 engaged with walls 40 of wells 15 of a multi-well plate 12, showing convex distal ends of fittings 28, and apertures 22.

Figure 16:
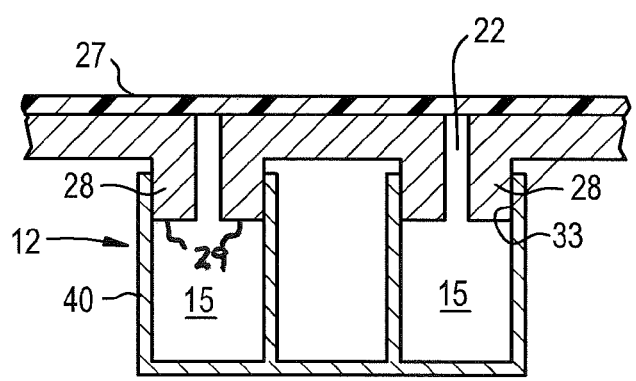
FIG. 16 is a cross-sectional view taken at line 15-15 of the lid shown in FIG. 15 engaged with a multi-well plate; and, FIGS. 17 A-D show evaporation and cell culture data for a multi-well plate covered by a lid, according to embodiments.

FIG. 15 is a perspective view of the underside of a lid 20 according to an embodiment, where the distal ends 29 of the fittings is flat and the fittings fit inside the well 15 of a multi-well plate. FIG. 16 is a cross-sectional view taken at line 15-15 of the lid shown in FIG. 15 engaged with a multi-well plate. FIG. 16 shows that, in embodiments, not every well of a multi-well plate has an associated aperture in the lid. Or, in the alternative, multi-well plates may have spaces between wells or may share well walls.

While the lid may have open apertures (as shown, for example, in FIG. 3), in some embodiments, a gas permeable or semipermeable membrane provides a physical barrier that maintains sterility within the wells of the plate and allows consistent gas exchange between the wells and the external environment. The semipermeable membrane also functions to uniformly minimize evaporation across the all of the wells of a multi-well plate, thereby eliminating the edge effect. In some of the illustrated embodiments, the semipermeable membrane mediates diffusion and evaporation through the lid without presenting an open aperture though which contaminants may enter the multi-well plate wells. In cell culture assays, for example, the culture media possesses certain physiological and chemical properties, including pH, oxygen and carbon dioxide concentrations, and temperature so as to support cell growth and proliferation.

Gases such as oxygen and carbon dioxide in the cell culture media are in a dissolved state. Oxygen is needed for cellular metabolism, though too high an oxygen concentration may be toxic due to the generation of free radicals. Carbon dioxide, which may be both a cellular metabolic byproduct and a nutrient, exists in many forms, such as carbonic acid ($H_2CO_3$) and mixtures of bicarbonate ($HCO_3^-$) and hydrogen ions.

Many cell cultures are carried out under atmospheric conditions (20-21% oxygen) supplemented with carbon dioxide (typically 0-10% to maintain media pH). However, oxygen concentrations in the body are much lower than in atmospheric air. For example, oxygen concentrations range from 0.5 to 7% in the brain; 1 to 5% in the eyes; 4 to 12% in the liver, heart, and kidneys; and 3 to 5% in the uterus. As a result, many studies have shown greater cell yield and function at oxygen levels below atmospheric levels (i.e., under hypoxic conditions).

In embodiments, the semipermeable membrane has a diffusion coefficient at 25° C. for oxygen and carbon dioxide of at least $0.1 \times 10^{-6}$ $cm^2 s^{-1}$.

In embodiments, the cross-sectional size (e.g., diameter) of each lid aperture 23 is less than the size of the opening of a corresponding well. In embodiments, a ratio of the lid aperture 23 area to the well opening area ranges from 5 to 99%, e.g., 5, 10, 20, 30, 40, 50, 60, 70, 80, 90, 95 or 99%, including ranges between any of the foregoing. In embodiments, the lid apertures 23 have a diameter of 0.005 to 0.05 inches, e.g., 0.005, 0.01, 0.015, 0.02, 0.025, 0.03, 0.035, 0.04, 0.045 or 0.05 inches, including ranges between any of the foregoing. The lid apertures 22 may be circular in shape; however, their shape may also be oval, square, rectangular, or triangular for example. As used herein, the size or diameter of the lid aperture 23 refers to the largest distance between edges of the opening, and use of the term "diameter" does not mean that the membrane must be circular.

The lid 20 can be made using conventional plastic or glass forming processes. If the lid is made from a plastic or polymeric material, the lid can be injection molded. The lid and the semipermeable membranes can be formed simultaneously, e.g., from the same material in a 1-shot molding process such as is illustrated in FIG. 2. Alternatively, the semipermeable membranes can be formed in a separate step such as by over-molding a membrane material into openings that are defined in the plate in a prior step and/or by providing a gas-permeable thin film over such openings such as is illustrated in FIGS. 3 and 4, respectively.

Referring back to FIG. 1 and FIG. 5, in embodiments, the lid 20 includes a raised peripheral rib 24 adapted to allow another multi-well plate to be stacked on top of the lid without obscuring the semipermeable membranes. According to certain embodiments, the height of the peripheral rib 24 may be at least about 0.025 inches.

In embodiments, the lid 20 further includes a skirt 26. In embodiments, the skirt can be short, medium or long. For example, the skirt may have a height that is approximately the same height as a standardized multi-well plate. This height is typically at least about 0.190 inches for a shallow lid and at least about 0.310 inches for a deep lid. Longer skirts are also contemplated.

As shown in FIGS. 3-9, lid 20 comprises a plurality of fittings 28 extending from the bottom surface 31 of main body 19. As shown also in FIGS. 10, 12 and 14, the fittings 28 extend perpendicularly from the bottom surface 31 of lid 20 and are positioned peripheral to openings 22. The fittings 28 are shaped and sized to frictionally engage with corresponding sidewalls 40 of wells of the multi-well plate 12. This engagement limits lateral (in-plane) and perpendicular (out-of-plane) movement of the lid when the lid covers the plate and helps to secure the lid in place, thus mitigating the likelihood of well-to-well cross-contamination. The fittings, which are aligned with the openings formed in the lid, minimize the rate of evaporation from the wells. The number, size and shape of the fittings, as well as their arrangement across the underside of the lid, depend on the multi-well plate used and, in particular, on the number, size, shape and arrangement of the wells in the plate. The plate may have any number of wells in any arrangement.

In embodiments, a multi-well plate lid comprises a planar main body having a top surface, a bottom surface, and a peripheral skirt extending downwardly from the main body and defining sidewalls thereof. Plural openings are provided in the main body and a semipermeable membrane is disposed over or at least partially within each opening. The semipermeable membrane comprises (i) a continuous thin film covering each of the openings, (ii) a locally-thinned portion of the main body, or (iii) a quantity of material at least partially filling each opening. An assay or cell culture device comprises a multi-well plate and such a lid.

The fittings and the planar main body of the lid may be of a unitary construction, i.e., the fittings are formed from the same material used to form the lid (i.e., simultaneously during the same lid-forming process). Alternatively, the fittings may be formed as separate entities (either from the same material or from a different material than the main body of the lid) and attached thereto. When the fittings are formed separately from the lid, they can be attached to the underside of the lid by use of a solvent-resistant adhesive, such as glue or double-sided adhesive tape. Example methods for forming and attaching the fittings to the lid include, but are not limited to injection molding, over-molding, thermoforming, vacuum forming, adhesive bonding, chemical bonding, thermal bonding, pressure bonding, mechanical bonding, ultrasonic welding, and combinations thereof. The fittings may be formed from a non-rigid, flexible material such as, for example, silicone, rubber, and neoprene. In embodiments, exposed surfaces of the fittings are non-wetting.

Disclosed is a semipermeable lid for a multi-well plate, the lid in various embodiments comprising a substantially planar body having top and bottom surfaces, a skirt extending downwardly from the perimeter of the body to form sidewalls, an array of fittings projecting from the bottom surface of the lid, the fittings configured to engage with inner surfaces of a respective well opening, or outer surfaces of a respective well opening, and a plurality of apertures formed in the body, each of the apertures, or a plurality of apertures, corresponding to a respective one of the fittings of the lid. In embodiments, the lid further comprises gas permeable membranes formed in or over the apertures which may be formed from the lid body material, or may comprise a different material. The semipermeable membranes may comprise a gas-permeable, non-wetting thin film.

The disclosed lid enables continuous and uniform gas exchange into and out of the wells of a multi-well plate, mitigates evaporation, and by providing a physical barrier, limits cross-contamination between wells, e.g., during plate agitation and shaking.

The lid is sturdy and easy to handle, e.g., manually or by automated equipment, reusable, suitable for high-throughput screening, and inexpensive to manufacture due to its design. The disclosed assay or cell culture device can, in turn, be used to culture bacteria, yeast, fungi and algae, and cells such as mammalian cells, plant cells and insect cells, for example.

In embodiments the device may further comprise a cover adapted to fit over the lid. The cover may include an array of openings that are aligned with the openings in the lid as well as a downwardly-extending skirt that forms sidewalls at the perimeter of the assembled device. The cover may be formed from ceramic, stainless steel or other metal such that during use the weight of the cover improves the seal between the lid and the microplate, e.g., during agitation.

Examples

Suspension culture of Sf9 cells were maintained in 125 mL shaker flask (Corning) in 30 mL Sf900-II medium (Life Technologies). Cultures were incubated at 28° C., without $CO_2$ control with constant agitation at ~125 rpm in an orbital shaker (15 mm orbit). For low evaporation lid studies, cells were seeded into 24-square deepwell plates (Corning Axygen) at ~0.5×10$^6$/mL viable cells in 3.0 mL medium. Cultures were incubated at 28° C., without $CO_2$ control with constant agitation at ~300 rpm in an orbital shaker (19 mm orbit). Viable cell density and percentage viability were assessed daily using a Vi-Cell™ analyzer (Beckman Coulter).

Data showing evaporation data and the effects of evaporation on the culture of Sf9 insect cells are shown in FIG. 17. The Sf9 cells were cultured under shaking conditions at 28° C. and 25-40% relative humidity in three vessels: (i) a 24-square deep well plate sealed with a lid according to embodiments shown in FIG. 16 (having a gas permeable film covering the apertures) (Lid), (ii) a 24-square deep well plate sealed with only a gas-permeable film (Film), and (iii) a 125-mL Erlenmeyer (shaker) flask with a vent cap (Sigma cat. no. CLS431143) (Flask).

Figure 17A:
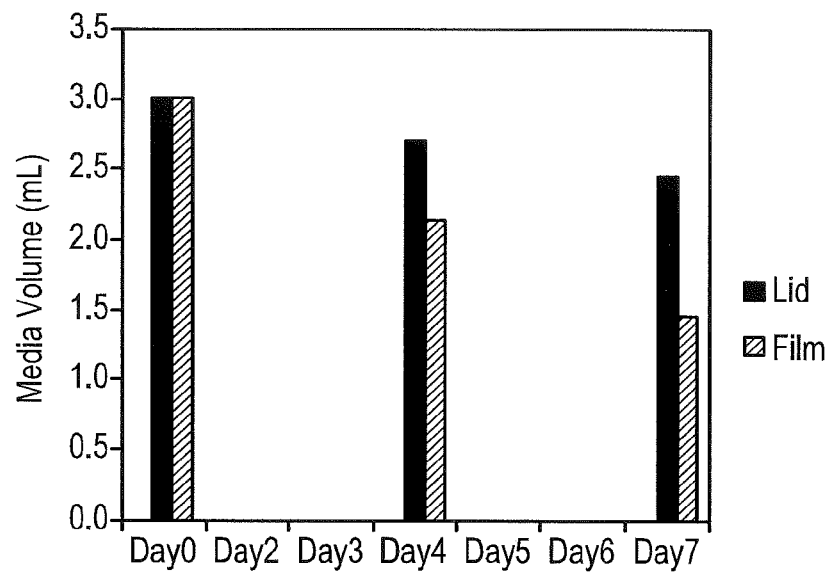

As shown in FIG. 17A, evaporation from a multi-well plate sealed with a lid made according to an example embodiment is significantly less than that from a multi-well plate sealed with a gas-permeable membrane, particularly when the plates are used inside an incubator over an extended period of time. For long-term cell culture applications, evaporation can significantly affect a wide range of parameters such as the total cell count, the average cell diameter, and the viable cell density, as shown in FIGS. 17B-D.

Figure 17B:
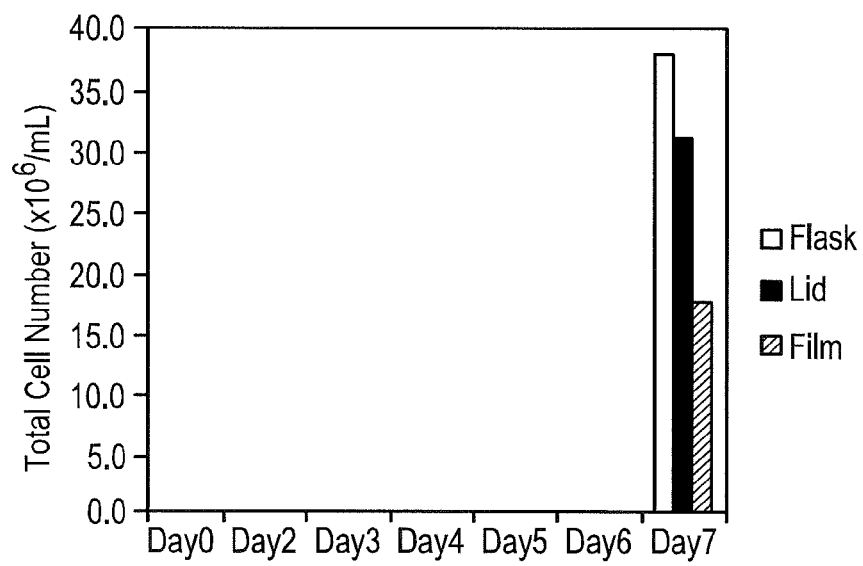
Figure 17C:
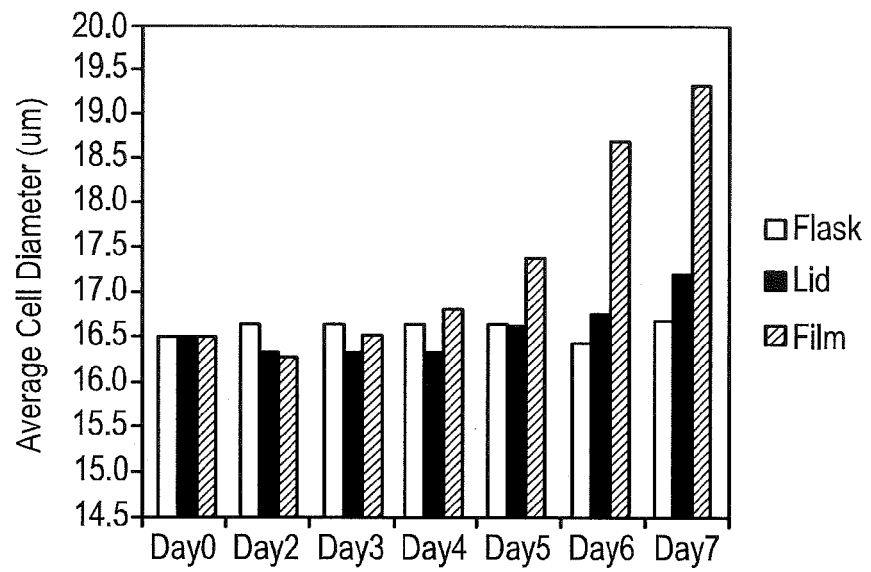
Figure 17D:
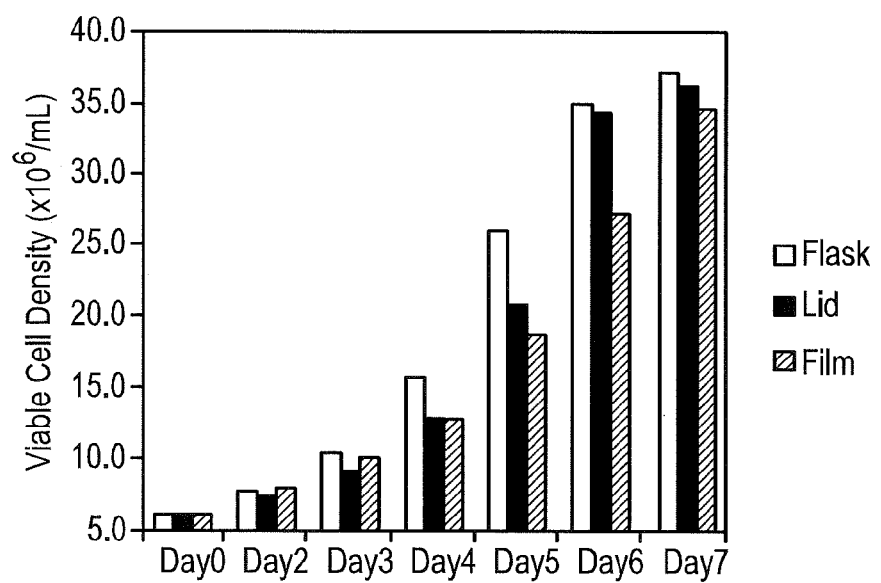

FIGS. 17B-D show that when Sf9 insect cells are cultured in a multi-well plate sealed with only a gas-permeable film, the increase in evaporation over time was accompanied by a marked decrease in the total cell number, a marked increase in the average cell diameter, and a slight decrease in the viable cell density. On the other hand, cells cultured in a multi-well plate sealed with a lid made according to embodiments in the present disclosure, showed comparable morphology and growth to cells cultured in a conventional flask equipped with a vent cap.

In a further experiment, different thin film membrane materials were evaluated. The gas diffusion performance of a polyurethane control film was compared to the performance for Trycite™ and TPX films for CHO cells cultured in deep well plates.

Suspension cultures of CHO cells were maintained in a 125 mL shaker flask in 30 mL CD OptiCHO medium (Life Technologies) supplemented with 8 mM Corning Glutagro™ and 10 mL/L HT (Hypoxanthine, Thymidine) (Mediatech, Inc.). Cultures were incubated at 37° C., 8% $CO_2$ with constant agitation at ~130 rpm in an orbital shaker (19 mm orbit). For low-evaporation lid evaluations, cells were seeded into 24-square deepwell plates (Corning Axygen) at ~0.15×10$^6$/mL viable cells in 2.5 mL medium. Cultures were incubated at 37° C., 8% $CO_2$ with constant agitation at ~225 rpm in a Minitron shaker incubator (50 mm orbit, Infors AG). Viable cell density and percentage viability were assessed daily using a Vi-Cell™ analyzer (Beckman Coulter).

While the cell data for the three membrane materials was comparable, notable differences were observed in the cell culture media with respect to the $CO_2$, $HCO_3^-$ and lactic acid concentrations. With reference to Table 1, the gas concentrations were significantly higher with respect to the control when either Trycite™ or TPX films were used, while the concentration of lactic acid in the cell culture media was negligible. The foregoing suggests a marked change in cell biology when Trycite™ and TPX films are used. In Table 1, the partial pressures of oxygen and carbon dioxide are measured in mmHg; the lactic acid content is measured in g/L; and the carbonate ion concentration is measured in mmol/L.

TABLE 1

| Samples in duplicate | pO₂ | pCO₂ | Lactic acid | HCO₃⁻ |
|---|---|---|---|---|
| Control | 165.20 | 30.45 | 3.02 | 5.05 |
| Trycite ™ film | 171.85 | 47.55 | <0.2 | 19.95 |
| TPX film - 25 μm | 165.45 | 50.25 | <0.2 | 33.60 |
| TPX film - 50 μm | 160.70 | 41.80 | <0.2 | 28.40 |

As used herein, the singular forms "a," "an" and "the" include plural referents unless the context clearly dictates otherwise. Thus, for example, reference to an "alignment feature" includes examples having two or more such "fittings" unless the context clearly indicates otherwise.

The term "include" or "includes" means encompassing but not limited to, that is, inclusive and not exclusive.

The term "affixed" or "attached" means that two parts are stuck to each other by any means known in the art including, for example, heat welding, laser welding, pressure welding, adhesive connections, injection molding, over-molding, thermoforming, vacuum forming, adhesive bonding, chemical bonding, thermal bonding, pressure bonding, mechanical bonding, and combinations thereof or other ways of connecting two parts together. "Affixed" or "attached" does not include using additional hardware to connect two parts together, such as using clamps, screws, bolts, clips or other hardware, unless specifically described.

"Optional" or "optionally" means that the subsequently described event, circumstance, or component, can or cannot occur, and that the description includes instances where the event, circumstance, or component, occurs and instances where it does not.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Integral" means made or manufactured as a single part and includes the single part as well as parts attached to the single part, when the parts are attached in a way that, under normal use, the parts would not be disassembled or separated from each other. For example, a lid having a semipermeable or gas permeable membrane attached to the lid is a unitary party. However, a part that can be disassembled (without breaking the part) into its component parts is not "unitary". For example a lid having a removable flexible gasket is not "unitary".

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" or "structured to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a semipermeable membrane comprising a non-wetting thin film include embodiments where a semipermeable membrane consists of a non-wetting thin film and embodiments where a semipermeable membrane consists essentially of a non-wetting thin film.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

We claim:

1. A multi-well plate lid comprising:
a unitary main body comprising:
a top surface;
a bottom surface; and
a plurality of apertures extending into the main body;
a gas permeable material extending across each of the plurality of apertures, wherein the gas permeable material selectively permits gases to pass through the gas permeable material while restricting the passage of liquids through the gas permeable material; and
a plurality of fittings extending from the bottom surface of the main body, each aperture of the plurality of apertures having an associated fitting of the plurality of fittings, each fitting comprising fitting walls and a distal face extending around each associated aperture, wherein a diameter of each aperture (Da) is smaller than a distance between the fitting walls (Df) of the associated fitting.

2. The lid according to claim 1 wherein each fitting of the plurality of fittings is sized to fit inside a well of a multi-well plate.

3. The lid according to claim 1 wherein each fitting of the plurality of fittings is sized to fit around the outside of a well of a multi-well plate.

4. The lid according to claim 2 wherein the distal faces of the fittings are concave, convex or flat.

5. The lid according to claim 1, wherein the gas permeable material comprises a continuous thin film covering the top surface of the main body of the lid.

6. The lid according to claim 1, wherein the gas permeable material comprises a discontinuous thin film covering at least one aperture of the plurality of apertures at the top surface of the main body of the lid.

7. The lid according to claim 1, wherein the gas permeable material comprises a plug of gas permeable material positioned within each aperture of the plurality of apertures.

8. The lid according to claim 5, further comprising a plug of gas permeable material positioned within each aperture of the plurality of apertures.

9. The lid according to claim 6, further comprising a plug of gas permeable material positioned within each aperture of the plurality of apertures.

10. The lid according to claim 1, further comprising a raised peripheral rib on the top surface of the main body structured to allow an additional multi-well plate to be stacked on top of the lid.

11. The lid according to claim 1, wherein the main body comprises stainless steel, glass, ceramic, or a polymer material selected from the group consisting of polystyrene, polymethylpentene, polypropylene, polyethylene, polytetrafluoroethylene, polycarbonate, and polyacrylate.

12. The lid according to claim 1 wherein the main body comprises a polymer material selected from the group consisting of polystyrene, polymethylpentene, polypropylene, polyethylene, polytetrafluoroethylene, polycarbonate, and polyacrylate.

13. The lid according to claim 12, wherein the gas permeable material comprises a locally thinned layer of the polymer material forming the main body, wherein the locally thinned layer comprises a thickness that is less than a thickness of the main body at positions outside of the locally thinned layer.

14. The lid according to claim 13, wherein the lid is a single-shot part comprising the same material throughout.

15. The lid according to claim 5, wherein the gas permeable material is selected from the group consisting of polystyrene, polymethylpentene, olytetrafluoroethylene, polycarbonate, polyacrylate, polyurethane, non-woven rayon, ethyl cellulose, perforated acetate and polyester.

16. The lid according to claim 6, wherein the gas permeable material is selected from the group consisting of polystyrene, polymethylpentene, olytetrafluoroethylene, polycarbonate, polyacrylate, polyurethane, non-woven rayon, ethyl cellulose, perforated acetate and polyester.

17. The lid according to claim 7, wherein the gas permeable material is selected from the group consisting of polystyrene, polymethylpentene, olytetrafluoroethylene, polycarbonate, polyacrylate, polyurethane, non-woven rayon, ethyl cellulose, perforated acetate and polyester.

18. The lid according to claim 8, wherein the gas permeable materials of the plugs of gas permeable material and the thin film are selected from the group consisting of polystyrene, polymethylpentene, olytetrafluoroethylene, polycarbonate, polyacrylate, polyurethane, non-woven rayon, ethyl cellulose, perforated acetate and polyester.

19. The lid according to claim 5, wherein the gas permeable material is different from the material forming the main body.

20. The lid according to claim 6, wherein the gas permeable material is different from the material forming the main body.

21. The lid according to claim 7, wherein the gas permeable material is different from the material forming the main body.

22. The lid according to claim 8, wherein the gas permeable materials of the plugs of gas permeable material and the thin film are different from the material forming the main body.

23. The lid according to claim 5, wherein the thin film comprises is a single-layer film or a multi-layer film.

24. The lid according to claim 6, wherein the thin film comprises is a single-layer film or a multi-layer film.

25. The lid according to claim 7, wherein the thin film comprises is a single-layer film or a multi-layer film.

26. The lid according to claim 8, wherein the thin film comprises is a single-layer film or a multi-layer film.

27. The lid according to claim 1 further comprising a polymer mesh positioned on the gas permeable material.

28. A lid and multi-well plate assembly comprising:
   a multi-well plate;
   a lid comprising:
      a unitary main body comprising:
         a top surface;
         a bottom surface; and
         a plurality of apertures extending into the main body;
      a gas permeable material extending across each of the plurality of apertures, wherein the gas permeable material selectively permits gases to pass through the gas permeable material while restricting the passage of liquids through the gas permeable material; and
      a plurality of fittings extending from the bottom surface of the main body, each aperture of the plurality of apertures having an associated fitting of the plurality of fittings, each fitting comprising fitting walls and a distal face extending around each associated aperture, wherein a diameter of each aperture (Da) is smaller than a distance between the fitting walls (DO) of the associated fitting.

29. The assembly according to claim 28, wherein the multi-well plate comprises an array of wells individually sealed with the lid.

* * * * *

UNITED STATES PATENT AND TRADEMARK OFFICE
CERTIFICATE OF CORRECTION

PATENT NO. : 10,625,264 B2
APPLICATION NO. : 15/054460
DATED : April 21, 2020
INVENTOR(S) : Yulong Hong et al.

Page 1 of 1

It is certified that error appears in the above-identified patent and that said Letters Patent is hereby corrected as shown below:

On the Title Page

On page 2, in Column 2, item (56), Other Publications, Line 1, delete "10/319,75" and insert -- 10/319,750 --, therefor.

In the Claims

In Column 17, Line 31, Claim 15, delete "olytetrafluoroethylene" and insert -- polytetrafluoroethylene --, therefor.

In Column 17, Line 36, Claim 16, delete "olytetrafluoroethylene" and insert -- polytetrafluoroethylene --, therefor.

In Column 17, Line 41, Claim 17, delete "olytetrafluoroethylene" and insert -- polytetrafluoroethylene --, therefor.

In Column 17, Line 47, Claim 18, delete "olytetrafluoroethylene" and insert -- polytetrafluoroethylene --, therefor.

In Column 18, Line 44 (approx.), Claim 28, delete "(DO" and insert -- (Df) --, therefor.

Signed and Sealed this
Thirtieth Day of June, 2020

Andrei Iancu
*Director of the United States Patent and Trademark Office*